United States Patent [19]

Cham

[11] Patent Number: 4,895,558
[45] Date of Patent: Jan. 23, 1990

[54] AUTOLOGOUS PLASMA DELIPIDATION USING A CONTINUOUS FLOW SYSTEM

[75] Inventor: Bill E. Cham, Upper Brookfield, Australia

[73] Assignee: University of Queensland, St. Lucia, Australia

[21] Appl. No.: 146,029

[22] Filed: Jan. 20, 1988

[51] Int. Cl.⁴ ............................................. A61M 1/03
[52] U.S. Cl. ...................................... 604/4; 210/645; 210/651; 422/44
[58] Field of Search ....................................... 604/4–6, 604/85; 436/13, 16; 422/44; 530/422, 830; 210/645, 651

[56] References Cited

U.S. PATENT DOCUMENTS

| | | | |
|---|---|---|---|
| 3,647,624 | 3/1972 | Evenson | 604/5 |
| 4,025,423 | 5/1977 | Stönner et al. | 210/638 |
| 4,350,156 | 9/1982 | Malchesky et al. | 604/6 |
| 4,647,280 | 3/1987 | Maaskant et al. | 604/4 |
| 4,696,670 | 9/1987 | Ohnishi et al. | 604/49 |

FOREIGN PATENT DOCUMENTS

| | | | |
|---|---|---|---|
| 2944138 | 6/1981 | Fed. Rep. of Germany. | |
| 3118072 | 11/1982 | Fed. Rep. of Germany. | |
| 3213390 | 10/1983 | Fed. Rep. of Germany | 604/4 |
| 2571971 | 4/1986 | France | 604/5 |
| 1116396 | 9/1984 | U.S.S.R. | 604/5 |

OTHER PUBLICATIONS

Agnese et al.; "Evaluation of Four Reagents for Delipidation of Serum"; Clinical Biochemistry (Ottawa), 16(2), pp. 98–100 (1983).

Parker et al.; "Plasma HDL is Increased when LDL is Lowered by LDL-Pheresis"; Proc. Nat. Acad. Sci. (USA); 83(3), pp. 777–781 (2-1986).

*Primary Examiner*—Dalton L. Truluck
*Attorney, Agent, or Firm*—Foley & Lardner, Schwartz, Jeffery, Schwaab, Mack, Blumenthal & Evans

[57] ABSTRACT

A method and apparatus for autologous plasma delipidation of animals (including humans). The method comprises drawing blood from the animal, separating the plasma from the red blood cells, delipidating the plasma with a lipid solvent, remixing the delipidated with the red blood cells and re-introducing the delipidated blood into the animal. A preferred apparatus which utilizes the above method comprises a needle for drawing blood from the animal and the blood is then fed into a centrifugal separator where the blood is separated into the plasma and red blood cells. The plasma is then mixed with a biphase solvent and passed through a separator where the delipidated plasma (in an aqueous phase) is drawn off from the lipid components (in an organic phase). After removal of solvent, the delipidated plasma is remixed with the red blood cells and re-introduced to the animal by a re-infusion needle.

8 Claims, 6 Drawing Sheets

AUTOLOGOUS PLASMA DELIPIDATION USING A CONTINUOUS FLOW SYSTEM

BACKGROUND OF THE INVENTION

This invention relates to a method of and apparatus for autologous plasma delipidation in animals (which term shall include humans) using a continuous flow system.

Cardiovascular diseases are responsible for more than half of all deaths in Australia and the United States and are frequent in most other industrialized countries. At present, an Australian or American male has a one in five risk of developing clinical evidence of coronary heat disease (CHD) before his 65th birthday.

One such disease is atherosclerosis which is characterised by focal fatty thickening in the inner aspects of large vessels supplying blood to the heart, brain and other vital organs. These lesions obstruct the lumen of the vessel and result in ischaemia of the tissue supplied by the vessel. Prolonged or sudden ischaemia may result in a clinical heart attack or stroke from which the patient may or may not recover.

It is believed that atherosclerosis begins in early childhood evolving through various stages before becoming clinically apparent in middle and late adult life. The earliest grossly recognizable intimal lesion is the fatty streak composed of lipid material, connective tissue and other substances. It is present in the aorta of many children less than 3 years of age. Fatty streaks become evident in the coronary arteries during the second decade, being seen in nearly all cases of CHD after 20 years of age. The frequency of coronary fatty steaks parallels the development of CHD. The most striking biochemical abnormality in human atherosclerosis is the accumulation of massive amounts of cholesteryl esters in the core of the atheromatous plaque.

The relationship between dietary lipid, serum cholesterol and atherosclerosis has long been recognised. In many epidemiological studies it has been shown that a single measurement of serum cholesterol has proved to be a significant predictor of the occurrence of CHD.

There seems little doubt concerning the relationship between elevations of plasma cholesterol and the development of premature CHD in humans. The fraction of cholesterol carried in low-density lipoproteins (LDL) appears to be particularly atherogenic. Thus, elevations of LDL and LDL-cholesterol apparently predispose individuals to an accelerated form of atherosclerosis.

As an individual grows larger and older, there is a net accumulation of cholesterol in body tissues, including the arterial wall. The body can rid itself of substantial quantities of cholesterol only through the liver, where cholesterol can be excreted in the bile and in the faeces. A mechanism has not yet been firmly established to explain how cholesterol from peripheral tissues, including the arterial wall, is transported to to the liver for removal. It has been suggested that high-density lipoprotein (HDL) plays a role in removing cholesterol from tissues and promoting reverse cholesterol transport to the liver.

Diet is the basic element of all therapy for hyperlipidaemia (excessive amount of fat in plasma). The use of diet as a primary mode of therapy requires a major effort on the part of physicians, nutritionists, dietitians and other health professionals.

If dietary modification is unsuccessful, drug therapy is an alternative. Several drugs, used singly or in combination, are available. However, there is no direct evidence that any cholesterol-lowering drug can be safely administered over an extended period.

Finally, a combination of both drug and diet may be required to reduce the concentration of plasma lipids. Hypolipidaemic drugs are therefore used as a supplement to dietary control.

Many drugs are effective in reducing blood lipids, but none work in all types of hyperlipproteinemia and they all have undesirable side-effects. There is no conclusive evidence that hypolipidaemic drugs can cause regression of atherosclerosis.

In view of the above, new approaches have been sought to remove LDL from the plasma of homozygotes and of those heterozygotes for whom oral drugs are not effective.

Plasmapheresis (plasma exchange) therapy has been developed and involves replacement of the patient's plasma with donor plasma or more usually a plasma protein fraction. This treatment can result in complications due to the possible introduction of foreign proteins and transmission of infectious diseases. Further, plasma exchange removes all the plasma proteins as well as VLDL, LDL and HDL and angiographic data suggest that HDL cholesterol is inversely correlated with the severity of coronary arterial lesions, as well as with the likelihood that these will progress. In the light of this, a technique designed to use the patient's own plasma and to conserve HDL during LDL removal would be desirable.

LDL apheresis can be achieved by various means, for example, by the absorption of LDL onto heparin-agarose beads (affinity chromatography) or the use of immobilized LDL-antibodies. Other methods presently available for the removal of LDL involve cascade filtration, absorption to immobilized dextran sulphate and LDL precipitation at low pH in the presence of heparin. Each method specifically removes LDL but not HDL.

LDL apheresis has, however, disadvantages. Significant amounts of other plasma proteins are removed during apheresis and to obtain a sustained reduction in LDL-cholesterol, LDL apheresis must be performed frequently (up to once weekly).

Therefore, there is still a need, using techniques other than diet and/or drug therapy, to achieve a reduction of plasma cholesterol and in particular LDL-cholesterol in homozygous familial hypercholesterolemia and heterozygous familial hypercholesterolemia patients.

In response to the above problems, the present inventor has developed a biphasic solvent system for extraction of biological solution which attains complete removal of cholesterol, triglyceride, phospholipid and non-esterified fatty acids from plasma without protein denaturation. In particular, the solvent system has the following advantages:

(i) delipidation is complete in a short period of time;
(ii) the treatment is mild enough so as not to affect ionic constituents or cause irreversible denaturation of proteins, including enzymes;
(iii) the proteins, including the apolipoproteins (defatting lipoproteins), remain soluble in an aqueous phase, while an organic phase contains the dissolved lipids;
(iv) the apolipoproteins dissolve lipids;
(v) recovery of the aqueous phase after extraction is simple and very efficient; and
(vi) the method is flexible i.e. it is applicable to small and large volumes of biological solutions as required.

In vitro studies have shown that a hyperlipaemic plasma—which looks turbid before delipidation—clears after delipidation using the above solvent system because the lipids are extracted from the plasma into an organic phase. The amount of lipid extracted from plasma can be measured after evaporation of the organic phase.

While the system discussed above has been successful in vitro in the experimental scale, it has not been suitable for the clinical delipidation of animal plasma.

SUMMARY OF THE INVENTION

It is an object of the present invention to upgrade the above discussed in vitro system to a clinical system wherein:

1. the application of a delipidation (defatting) procedure prevents, ameliorates and reverses atherosclerosis (fatty thickening in the inner aspects of large vessels supplying blood to the heart, brain and other vital organs) to animals, including humans;
2. the clinical procedure is non-toxic; and
3. other substances such as fat-soluble vitamins which are removed by the defatting procedure are reintroduced to the subject.

A further object is to develop an apparatus that will be able to defat blood plasma in a continuous mode.

In one aspect, the present invention provides a method for autologous plasma delipidation of an animal using a continuous flow system, said method comprising:
(a) drawing blood from the animal;
(b) separating the plasma from the red blood cells;
(c) delipidating the plasma with a lipid solvent;
(d) remixing the delipidated plasma with the red blood cells; and
(e) re-introducing the delipidated blood into the animal.

Preferably the delipidation step comprises:
(i) mixing the plasma with the liquid solvent;
(ii) allowing the mixture to separate into an organic solvent/lipid phase and an aqueous delipidated plasma phase; and
(iii) drawing off the organic phase.

In a second aspect, the present invention provides an apparatus for autologous plasma delipidation of an animal, said apparatus comprising:
(a) means to draw blood from an animal;
(b) means to separate the plasma from the red blood cells;
(c) means to delipidate the plasma using a lipid solvent;
(d) means to separate the delipidated plasma from the solvent;
(e) means to remix the delipidated plasma with the red blood cells; and
(f) means to re-introduce the delipidated blood into the animal.

Preferably, the apparatus is based on a double centrifuge blood cell separation machine wherein the blood is drawn from the animal via a drawing needle and the blood is mixed with a prime solution (and anticoagulant) and fed to a first centrifugal separator where the blood is separated into the plasma and red blood cells. The plasma may then be fed to container of solvent or the plasma and solvent may be mixed in continuous flow lines. After mixing the plasma and the solvent, the mixture is preferably passed through a primary separator where the denser delipidated plasma (in an aqueous phase) is drawn off below the solvent/lipid components (in an organic phase). The plasma is passed through a second centrifugal separator to remove any remaining traces of solvent before the delipidated plasma is remixed with the red blood cells and re-introduced to the animal e.g. by a re-infusion needle.

The lipids may be extracted from the solvents e.g. by distillation of the solvent and the solvent recycled through the apparatus.

The preferred solvent is DIPE (di-isopropylether) which is preferably peroxide free, which may be mixed with butanol, 1-pentanol and/or 1-hexanol in the range 25%:50% to 50%:50%(V/V). The most preferred solvent is butanol-DIPE 40%:60%(V/V).

BRIEF DESCRIPTION OF THE DRAWINGS

To enable the invention to be fully understood, preferred embodiments will now be described with reference to the accompanying drawings, in which.

DETAILED DESCRIPTION OF THE PREFERRED EMBODIMENT

The influence of plasma delipidation was studied in two dogs (one normocholesterolaemic and the other hypercholesterolaemic).

Approximately one-third of the blood volumes of the dogs were removed. The red blood cells were removed from the plasma by centrifugation. The plasma was delipidated, then remixed with the red blood cells and re-introduced back into the original dog by intravenous infusion. Blood samples were collected before and after this delipidation procedure for biochemical, haematological and lipid analyses.

Figure 1:
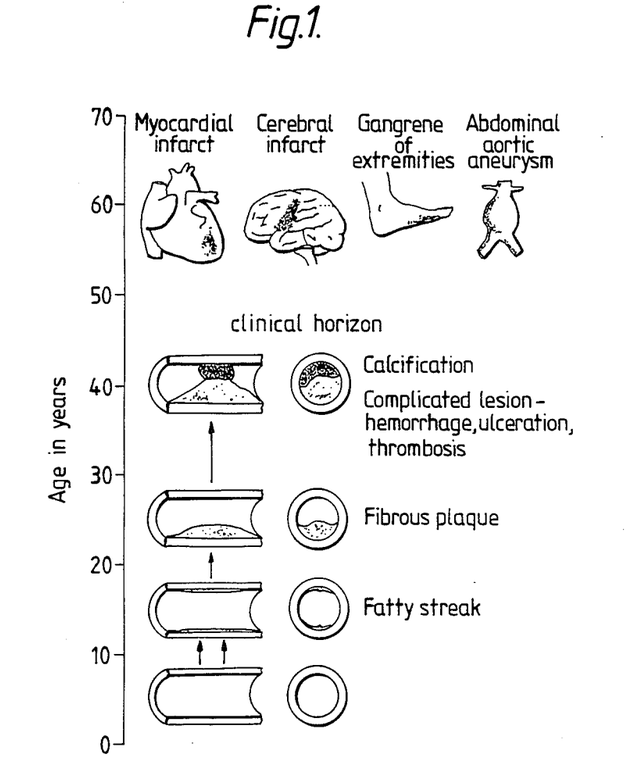
FIG. 1 shows the build-up of deposits in the aorta of a human with age.
Figure 2:
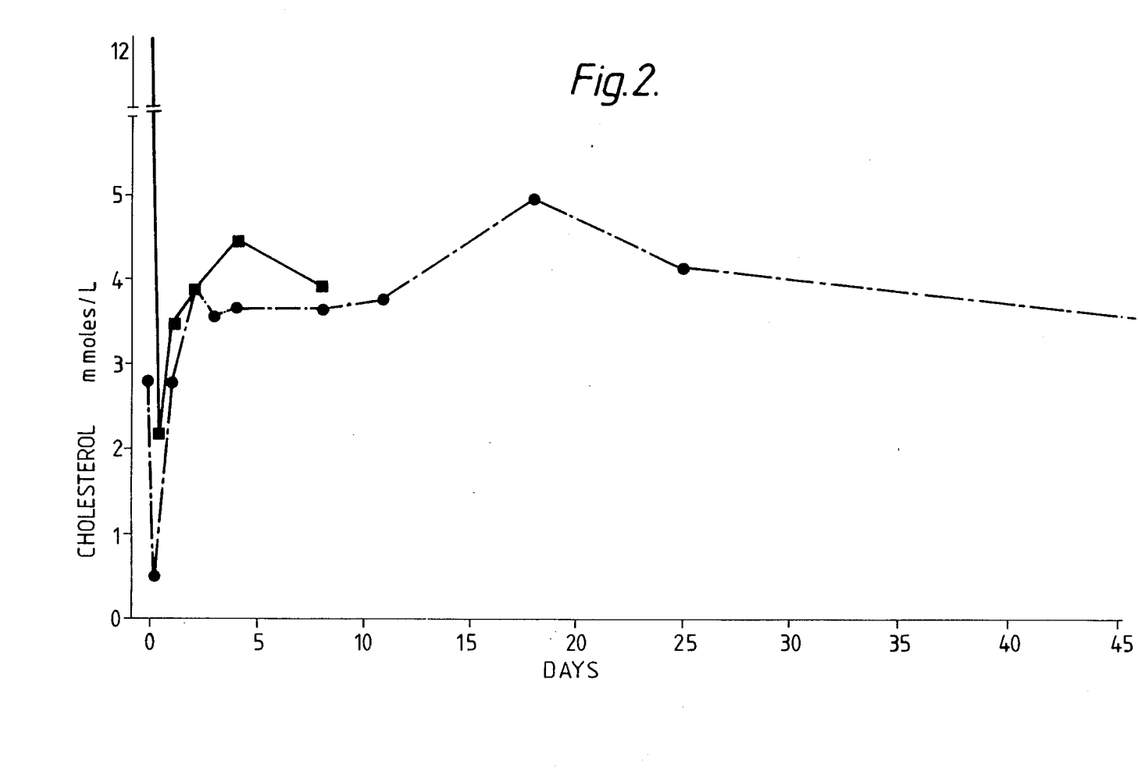
FIG. 2 is a graph of the level of cholesterol with time in two dogs treated in accordance with the present invention.

During the first 15 minutes after the intravenous infusion of the autologous delipidated plasma, a low level of cholesterol was detected in the dogs, which increased in 1 hour to approximately the initial level in the normocholesterolaemic dog (FIG. 2, circles). However, in the hypercholesterolaemic dog the plasma cholesterol level did not return to its initial level during the following eight days (FIG. 2, squares).

One hour after reinfusion of the delipidated plasma, the plasma cholesterol concentration in the initially hypercholesterolaemic and normocholesterolaemic dogs remained within the normal range (3.24–6.48 mmol/l) and remained unchanged over the experimental period.

During the experimental period there were no changes in the following biochemical and haematological parameters:

| Biochemical | Haematological |
| --- | --- |
| Bilirubin | WBC |
| Total protein | RBC |
| Albumin | Haemaglobin |
| Total globulin | Hct |
| alpha$_1$, alpha$_2$, beta | MCV |
| and gamma globulins | MCH |

| Biochemical | Haematological |
|---|---|
| Sodium | MCHC |
| Potassium | Polymorphs |
| Chloride | Lymphocytes |
| Total Carbon dioxide | Monocytes |
| Calcium | Eosinophils |
| Phosphate | Platelets |
| Urea | |
| Urate | |
| Creatinine | |
| Alkaline Phosphatase | |
| Lactate dehydrogenase | |
| Aspartate transaminase | |
| Creatine hinase | |
| Amylase | |
| 5' Nucleotidase | |
| Gamma-glutamyl transpeptidase | |
| Anion gap | |
| Alpha$_1$ Antitrypsin | |

In addition to earlier in vitro research on the biphasic solvent system which established that the delipidation of plasma does not affect the concentrations of the ionic constituents, proteins, pH and enzyme activities, additional work has now been undertaken on clotting factors. The results of that research are presented in the following Table 1.

TABLE 1

| Effect of plasma delipidation with BuOH-DIPE (40:60 V/V) on clotting factors | | |
|---|---|---|
| | Delipidation Time | |
| | 20 minutes | 30 minutes |
| Prothrombin time | unaffected | up 247% |
| Activated partial thromboplastin time | unaffected | up 239% |
| Clottable fibrinogen concentration | unaffected | down 40% |
| Total fibrinogen concentration | unaffected | down 59% |

As it will be seen, delipidation for 20 minutes does not affect prothrombin time (P.T.), activated partial thromboplastin time (A.P.T.T.), thrombin clotting time (T.C.T.), clottable fibrinogen (FIB.C) and total fibrinogen as measured by heat lability (FIB.H). Delipidation for 30 minutes partially affects all the clotting factors studied. Approximately 60% of the activity of clottable fibrinogen is lost and approximately 40% of the heat labile fibrinogen is lost.

It should be noted that delipidation of plasma for 20 minutes results in removal of all cholesterol and triglyceride but not phospholipids. Delipidation for 30 minutes removes all phospholipids from plasma.

It is known that removal of all lipoprotein fractions from plasma by ultracentrifugation has the same effect on blood clotting factors as the removal of lipid from plasma by delipidation with butanol-DIPE. This suggests that the effect of the present solvent system on clotting factors is by removal of phospholipids which play a crucial role in blood coagulation by specifically accelerating some of the reaction steps leading to clot formation.

From these experiments, it appears that delipidation of autologous plasma results in removal of lipids. The extracted plasma when reinfused into the animal picks up lipids, in particular, cholesterol, possibly from body stores. The procedure does not appear to have adverse effects on haematological and biochemical constituents. The animals appeared to be physically unaffected by the treatment.

In this connection using the butanol-DIPE solvent system, it has recently been shown that partial delipidation of human LDL (removal of 98% cholesterol, 95% triglyceride and 50% phospholipid) did not effect the binding activity of this treated LDL to cultured human fibroblasts when compared with untreated LDL. Moreover, delipidated LDL did not stimulate cholesteryl ester synthesis. On the other hand, many investigators using the butanol-DIPE system, have subsequently shown that cellular sterol synthesis is highly stimulated by delipidated serum. More recently it has been shown that this stimulatory effect may be caused by delipidated HDL which is present in delipidated serum. The induction is thought to be caused by removal of cellular sterol by apo-HDL. When an acceptor of cholesterol (apo-HDL) is present in the medium, macrophages excrete massive amounts of cholesterol. Substances in the delipidated d 1.215 g/ml fraction of plasma were shown to remove cholesterol from macrophages. Albumin and globulins did not accept large amounts of cholesterol. It was suggested that apolipoproteins (especially api-A-I) may have been responsible for the activity of this fraction.

With respect to atherosclerosis, the infusion of delipidated plasma may prove useful in an attempt to induce rapid endothelial repair by inhibition of the proliferative response. Partly delipidated plasma in the vascular system may inhibit cellular intake of cholesterol (by binding cholesterol-depleted LDL) and at the same time facilitate reverse cholesterol transport (increased cholesterol efflux by reducing cellular sterol content with delipidated HDL). Lipoprotein lipases and lecithin cholesterol acyltransferase may also be activated by their apolipoprotein cofactors.

Atherosclerosis can also be defined as a disease process that occurs when the influx and deposition of cholesterol into the arterial wall exceeds the egress of cholesterol from the arterial wall. This process is characterized by early deposition of cholesterol in and around arterial wall cells. The cholesterol is derived from certain types of lipoproteins. While these lipoproteins deliver cholesterol to the arterial wall cells, other types of plasma lipoproteins may be capable of removing cholesterol from the cells and transporting the cholesterol to the liver from excretion from the body.

Figure 3:
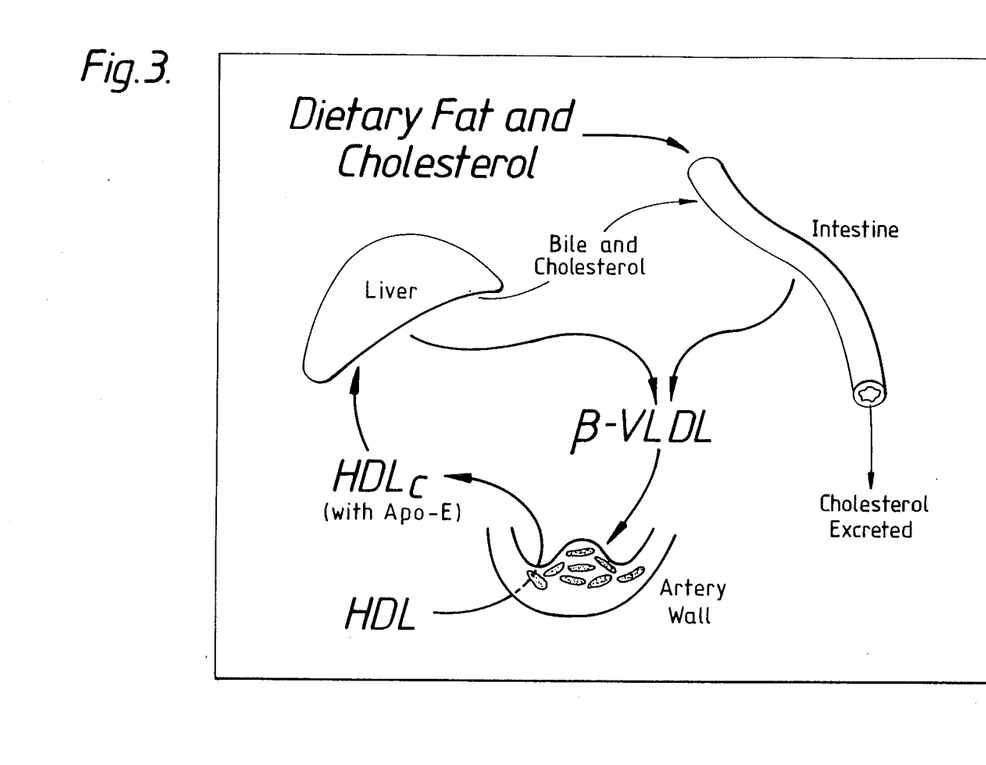
FIGS. 3 and 4 are graphs of the mechanism which leads to the build up of cholesterol in the arteries.

Foam cells, which accumulate cholesterol in the arterial wall, are thought to originate from smooth cells and/or macrophage monocytes. Studies have demonstrated that cholesteryl ester accumulation in macrophages is caused by the uptake of diet-induced beta-VLDL, and that the degree of this accumulation is modulated by the presence of HDL. It was suggested that the level of lipoproteins capable of delivering cholesterol to macrophages (i.e. beta-VLDL) versus the level of lipoproteins capable of acquiring cholesterol from the cells (i.e. HDL) may determine whether or not atherosclerosis develops in the in vivo situation (see FIG. 3).

The preliminary studies in dogs have shown that it is possible to extract lipids, in particular cholesterol, from plasma without effecting other plasma substances. This observation is of utmost importance and is the key to the clinical application. It has also been shown that the delipidated plasma (in particular apo-HDL) is capable of dissolving lipids including cholesterol. These phenomena may explain the observation that when autologous delipidated plasma is reinfused into the animal a decline in plasma cholesterol is first observed (because of the removal of cholesterol). It is quite feasible that the delipidated plasma (in particular api-HDL as shown by in vitro studies) dissolves and binds cholesterol which had previously been deposited in tissues. This explanation is to a certain extent enforced by the in vivo dog studies (15 minutes after reinfusion of the delipidated plasma, the delipidated plasma gradually picks up cholesterol until the plasma level of cholesterol reaches its normal level). If this cholesterol is dissolved from atherosclerotic plaques one would expect regression of atherosclerosis to occur.

Figure 4:
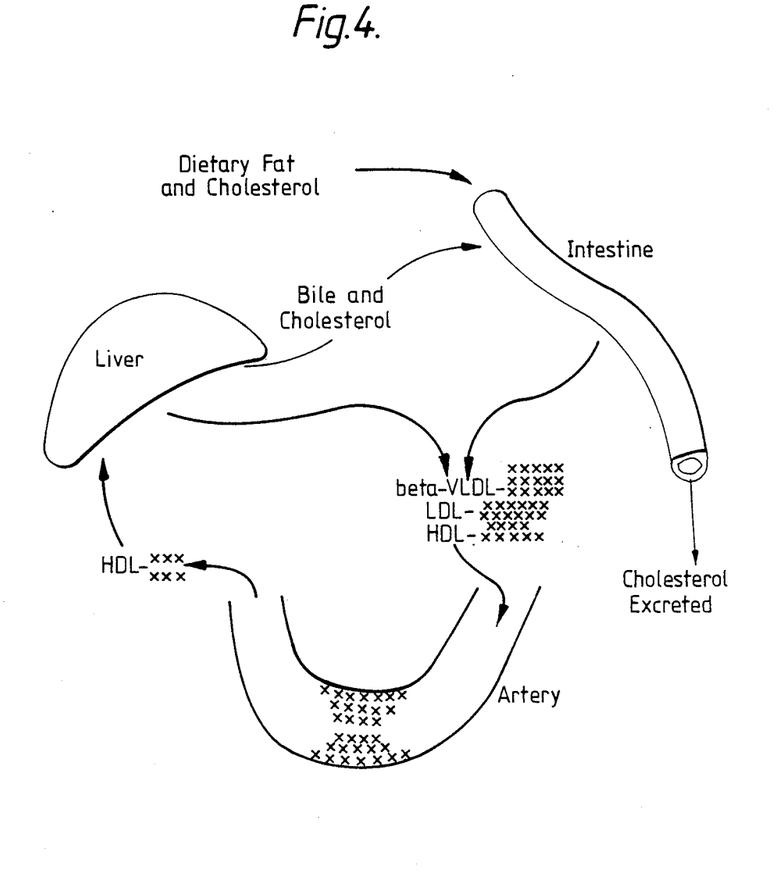
Figure 5:
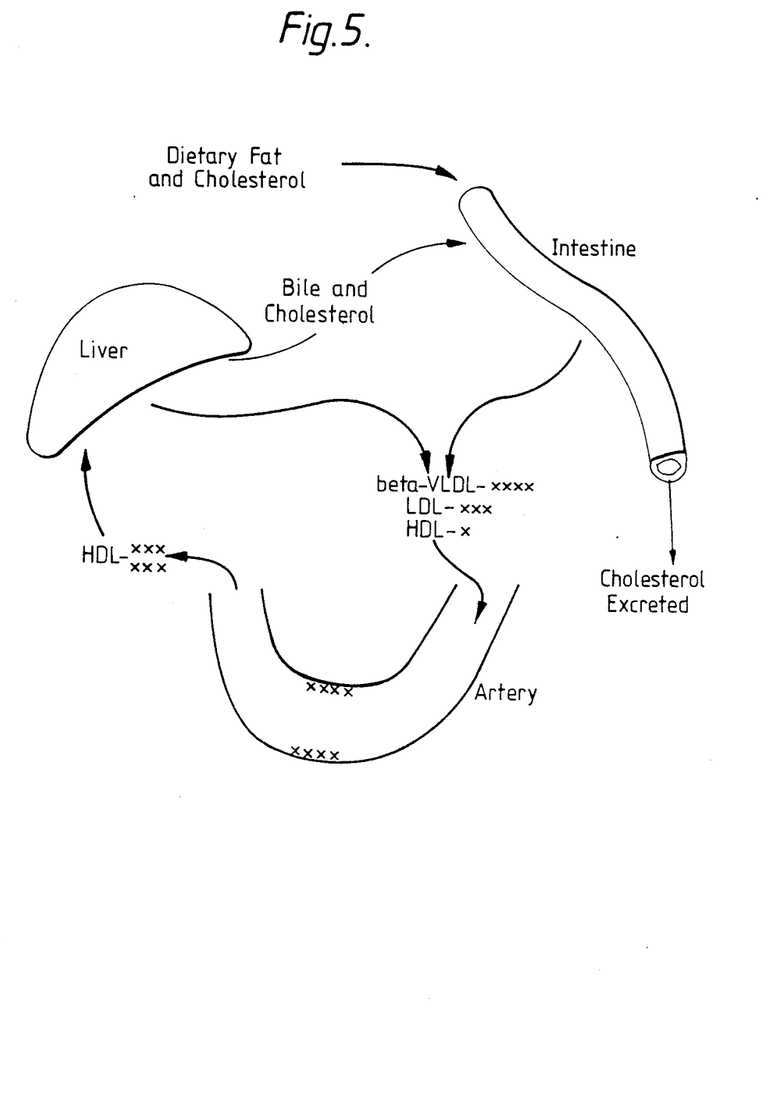
FIG. 5 is a graph of the mechanism which is believed to occur by the present invention which removes the cholesterol from the arteries.

The occurrence of atherosclerosis progresses when the influx of cholesterol into the arterial wall exceeds the level of egress from this tissue (FIG. 4). LDL and diet-induced beta-VLDL, which are cholesterol-rich lipoproteins, have been shown to deliver large amounts of cholesterol to macrophages in vitro and have been implicated in arterial disease in animals in vivo. The role of HDL in reverse cholesterol transport from cells of the arterial wall to the liver with subsequent excretion through the bile into the intestine is also shown. The crosses depict cholesterol carried by the lipoprotein fractions and the deposited cholesterol in the artery (FIG. 4). FIG. 5 shows the possible effects of the removal, delipidation and reinfusion of plasma in a continuous mode in the body system. The crosses depict cholesterol carried by the lipoprotein fractions and the deposited cholesterol in the artery. Delipidation of plasma results in reduction of cholesterol in the lipoprotein fractions. The cholesterol-depleted LDL and beta-VLDL can still bind to receptors. On the one hand, atherosclerosis will be partly or completely arrested because the influx of cholesterol into the arterial wall is reduced. On the other hand, the egress of cholesterol from the arterial plaque is increased by the cholesterol-depleted HDL.

Cholesterol-depleted HDL is capable of dissolving and binding cholesterol (see earlier). In this connection one would expect that as a consequence of plasma delipidation the cholesterol-depleted HDL will dissolve cholesterol from the atherosclerotic plaque. This cholesterol which is now HDL-bound is then taken to the liver (reverse cholesterol transport) which may then be excreted through the bile and intestine in the faeces. Thus reinfusion of autologous plasma results in a REDUCTION of INFLUX of cholesterol into the arterial wall and an INCREASE of EGRESS of cholesterol from this tissue (regression of autherosclerosis).

Because autologous plasma is used (the patient's own plasma is reintroduced) there will be no problems of rejection or antibody production.

Another beneficial effect of plasma delipidation is removal of adipose tissue (triglycerides) from the body. This procedure may also be applicable for detoxifying the body from fat-soluble toxins such as some herbicides and insecticides e.g. 2,4-D; 2,4,5T and the organo phosphates.

It may also be possible to use the present method to treat, or at least arrest, the spread of cancer.

The quickly-dividing cancer cells require lipids to produce the membranes for the newly generated cells. By removing the lipids from the plasma, the necessary building blocks for the cancer cells may be removed and so the mature cancer cells may die without dividing. Even if the cells do divide, the absence (or low level) of the lipids will reduce the rate of division arresting or retarding the rate of the spread of the cancer cells.

Figure 6:
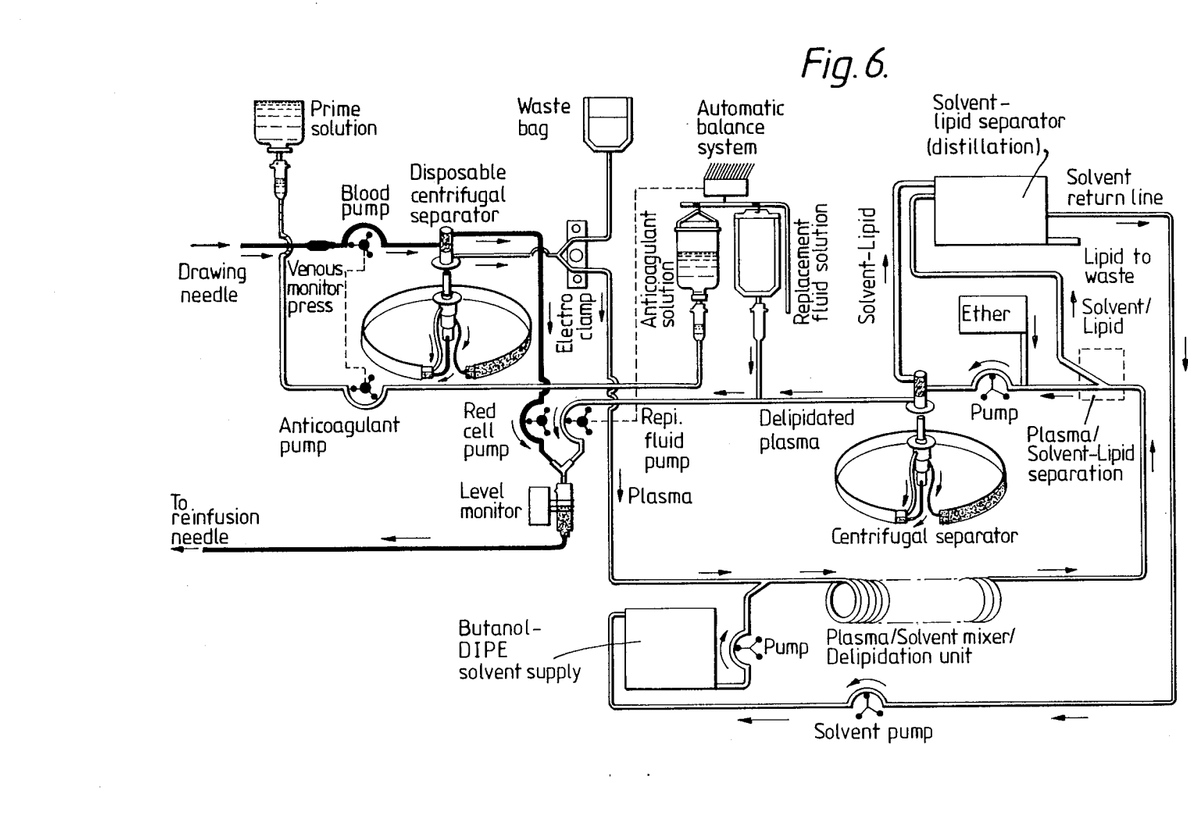
FIG. 6 is a schematic view of an apparatus constructed in accordance with the present invention.

Referring to FIG. 6, a schematic view of a machine suitable for the invention, the blood from the animal is drawn via a drawing needle and is mixed with an anticoagulent solution, drawn from a supply container via a metering pump.

The mixture passes through a vein monitor, drawn by a blood pump, and is fed to a first disposable centrifugal separator where the blood is separated into red blood cells, plasma and waste products (the latter being collected in a waste bag). The red blood cells are drawn through a red cell pump to a level monitor to be mixed with the delipidated plasma, supplied by the replacement fluid pump, for return to the animal via the reinfusion needle.

The plasma is mixed with butanol-DIPE (40%:60%V/V) solvent drawn from a supply via a solvent pump. The plasma and solvent is mixed and the solvent removes the lipids from the plasma. The mixture is then passed through a plasma/solvent lipid separation unit where most of the solvent-lipid combination (in the organic phase) is removed from the plasma (in the aqueous phase) In a simple laboratory experimental unit, the separation unit comprises a glass tubing unit with a Y-shape with the arms of the Y vertically aligned. Most of the solvent and lipid, in the less dense organic phase, flows out through upper arms while the plasma in the aqueous phase flows out through the lower arms. Ether, which breaks down any emulsion in the plasma and which removes any remaining solvent from the plasma is added after the separation unit. The plasma is then pumped through a second disposable centrifugal separator where the balance of the solvent and lipids (and the ether) (all in the organic phase) are removed and directed to a collector. (The solvent is distilled off from the lipid and the solvent is pumped back to the solvent supply tank in a recycling circuit, the lipids being directed to waste).

The now delipidated plasma is drawn by the fluid replacement pump to be mixed with the red blood cells. (A replacement fluid may be added (as required) to the plasma to overcome any loss in bulk of the plasma during the delipidation and separation steps).

As the patient's own blood is used during the method, and no drugs or foreign tissue is introduced, there should be no rejection of the delipidated blood by the body and there should be no adverse side effects.

The solvent acts to "wash" the lipids from the plasma.

As previously described with reference to FIG. 2, the lipid levels in the blood drop when the delipidation method is effected but rise again after e.g. 3 days apparently due to the stored lipids in the animals body entering the blood stream (see also FIGS. 4 and 5). By repeating the delipidation method at intervals, the build up of lipids in the arteries and other organs can be reversed and the likelihood of heart attacks or strokes reduced. As also discussed, the method can be repeated to remove fat-soluble toxins from the body.

The embodiments are described by way of illustrative examples only and various changes and modifications may be made thereto without departing from the present invention defined in the following claims.

We claim:

1. A method for the clinical removal of cholesterol and triglycerides from plasma of a living animal using a continuous flow system, comprising the steps of:

(a) drawing whole blood from a living animal;
(b) separating plasma from red blood cells of said blood;
(c) treating said plasma with a liquid lipid solvent, said solvent comprised of about 60% peroxide-free DIPE and about 40% butanol by volume, said treatment comprising
 (i) mixing, for a period of less than 30 minutes, said lipid solvent with said plasma to produce a mixture;
 (ii) allowing said mixture to settle into an organic solvent-lipid phase and an aqueous plasma phase; and
 (iii) separating said aqueous plasma phase from said organic phase;
(d) removing residual organic solvent from said aqueous plasma phase with ether to produce modified plasma;
(e) remixing said modified plasma with red blood cells of said animal to produce a blood product; and
(f) reintroducing said blood product into said animal, whereby said blood product is not characterized by protein denaturation or adverse effects on hematological and biochemical constituents thereof, including phospholipids and clotting factors, and has a lower content of cholesterol and triglycerides than said whole blood.

2. A method as defined in claim 1 wherein:
 (i) an anti-coagulent is mixed with the blood before separation; and
 (ii) a replacement fluid solution is added to the delipidated plasma to maintain the blood bulk.

3. A method as defined in claim 1 wherein: the organic solvent is separated from the lipids by distillation and is recycled.

4. An apparatus for the clinical removal of cholesterol and triglycerides from plasma of a living animal using a continuous flow system, said apparatus comprising the following parts operatively attached to each other:
 (a) a first means for drawing whole blood from a living animal;
 (b) a second means for separating plasma from red blood cells of said blood;
 (c) a third means for treating said plasma with a liquid lipid solvent, wherein said solvent comprises about 60% peroxide-free DIPE and about 40% butanol by volume, said treatment comprising
  (i) mixing, for a period of less than 30 minutes, said lipid solvent with said plasma to produce a mixture;
  (ii) allowing said mixture to settle into an organic solvent-lipid phase and an aqueous plasma phase; and
  (iii) separating said aqueous plasma phase from said organic phase;
 (d) a fourth means for delivering said solvent to said third means;
 (e) a fifth means for removing residual organic solvent from said aqueous plasma phase with ether to produce modified plasma;
 (f) a sixth means for remixing said modified plasma with red blood cells of said animal to produce a blood product; and
 (g) a seventh means for reintroducing said blood product into said animal,
whereby said blood product is not characterized by protein denaturation or adverse effects on hematological and biochemical constituents thereof, including phospholipids and clotting factors, and has a lower content of cholesterol and triglycerides than said whole blood.

5. An apparatus according to claim 4, wherein said second means comprises a first centrifugal separator.

6. An apparatus according to claim 4, wherein said fifth means comprises a second centrifugal separator.

7. An apparatus according to claim 4, further comprising an eighth means for adding a replacement fluid solution to said delipidated plasma to maintain blood bulk.

8. An apparatus according to claim 4, further comprising
 (a) a ninth means for separating said solvent from said organic solvent-lipid phase to produce a lipid-depleted solvent; and
 (b) a tenth means for pumping said lipid-depleted solvent to said solvent supply for recycling.

* * * * *